United States Patent
Xia et al.

(10) Patent No.: US 12,016,718 B2
(45) Date of Patent: Jun. 25, 2024

(54) APPARATUS AND METHODS FOR IMAGE QUALITY IMPROVEMENT BASED ON NOISE AND DOSE OPTIMIZATION

(71) Applicant: CANON MEDICAL SYSTEMS CORPORATION, Tochigi (JP)

(72) Inventors: Ting Xia, Vernon Hills, IL (US); Liang Cai, Vernon Hills, IL (US); Jian Zhou, Vernon Hills, IL (US); Zhou Yu, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 294 days.

(21) Appl. No.: 17/692,697

(22) Filed: Mar. 11, 2022

(65) Prior Publication Data
US 2023/0284997 A1  Sep. 14, 2023

(51) Int. Cl.
*A61B 6/00* (2024.01)
*A61B 6/02* (2006.01)
*A61B 6/03* (2006.01)
*G06T 11/00* (2006.01)

(52) U.S. Cl.
CPC ............ *A61B 6/544* (2013.01); *A61B 6/5258* (2013.01); *G06T 11/008* (2013.01); *A61B 6/025* (2013.01); *A61B 6/032* (2013.01); *G06T 2200/04* (2013.01); *G06T 2210/41* (2013.01)

(58) Field of Classification Search
CPC ....... A61B 6/544; A61B 6/5258; A61B 6/025; A61B 6/032; A61B 6/488; A61B 6/542; G06T 11/008; G06T 2200/04; G06T 2210/41; G06T 11/005; G06T 11/006
See application file for complete search history.

(56) References Cited

U.S. PATENT DOCUMENTS

| | | | |
|---|---|---|---|
| 2014/0233692 A1 | 8/2014 | Case et al. | |
| 2014/0270053 A1 | 9/2014 | Larson | |
| 2015/0282778 A1* | 10/2015 | Kato | G06T 11/005 378/5 |
| 2020/0094074 A1 | 3/2020 | Chen et al. | |

OTHER PUBLICATIONS

Paras Lakhani et al. "Machine learning in radiology: applications beyond image interpretation." American College of Radiology, 2017.

* cited by examiner

*Primary Examiner* — Courtney D Thomas
(74) *Attorney, Agent, or Firm* — Oblon, McClelland, Maier & Neustadt, L.L.P.

(57) ABSTRACT

A method, apparatus, and computer-readable storage medium for controlling exposure/irradiation during a main three-dimensional X-ray imaging scan using at least one spatially-distributed characteristic of a pre-scan/scout scan preceding the main scan. The at least one spatially-distributed characteristic includes (1) a spatially-distributed noise characteristic of the pre-scan and/or (2) a spatially-distributed identification of exposure-sensitive tissue types. The at least one spatially-distributed characteristic can be calculated from images reconstructed from sinogram/projection data and/or from sinogram/projection directly using a neural network.

20 Claims, 17 Drawing Sheets

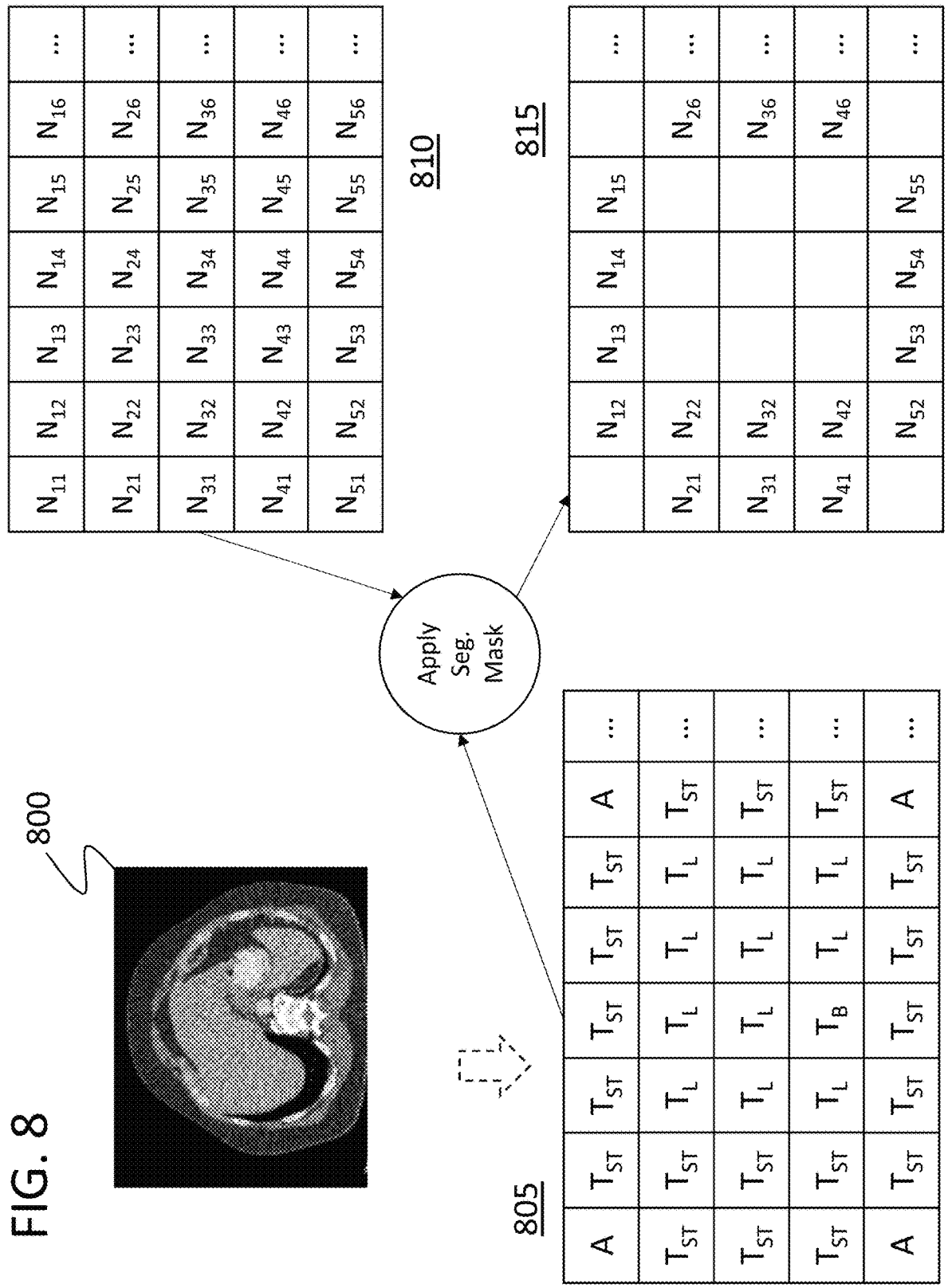

APPARATUS AND METHODS FOR IMAGE QUALITY IMPROVEMENT BASED ON NOISE AND DOSE OPTIMIZATION

BACKGROUND

Field of the Disclosure

The present disclosure relates to a method, apparatus, and non-transitory computer-readable storage medium for image quality improvement based on noise and dose optimization.

Description of the Related Art

In computed tomography (CT) imaging, imaging protocols impact image quality and radiation dose during many CT scans. Imaging protocols can include a myriad of imaging parameters (including scan acquisition parameters such as gantry rotation time, tube current, tube voltage, pitch, a field of view, and contrast agent timing), as well as image reconstruction parameters (such as reconstruction kernels, reconstruction algorithms, matrix size (e.g., 512, 1024), slice thickness), and patient-size dependent parameters—which affect the ultimate resulting image quality. Given the breadth of parameters that can be modified, general practice dictates that certain universally applicable values of each parameter be implemented in order to make the task practicable. For example, different anatomies of a patient body can be set with different exposures depending on the image protocols being utilized.

Medical imaging using ionizing radiation, such as X-rays, is known to increase cancer risks with increasing exposure to the ionizing radiation. A number of diagnostic medical imaging modalities and applications utilize ionizing radiation, including radiography, mammography, computed tomography (CT), nuclear medicine, and other forms of molecular imaging. In addition to diagnostic applications, ionizing radiation may be used in therapeutic radiology for treatment of patients with various forms of cancer. Collectively, these diagnostic and therapeutic medical applications pose risks that must be justified through risk-benefit analyses to substantiate the medical efficacy of use.

Thus, while radiation safety and medical imaging quality may be viewed in isolation, reality dictates that they are often directly related to one another. A given medical imaging procedure (e.g., abdominal CT examination) can be associated with a quantifiable amount of ionizing radiation, which is dependent upon the scan acquisition parameters selected, the technology utilized, and various attributes of the patient for which the examination is being performed. If one were to attempt to adjust the scan acquisition parameters in an attempt to reduce radiation dose, the overall image quality would be concurrently impacted, largely due to increased pixel noise and/or quantum noise. As a result, attempts to modify radiation dose (i.e., to improve radiation safety) without determining the resultant impact on image quality can be misguided. Radiation dose and image quality are inextricably related to one another and, as a result, should be considered in combination.

Such considerations of the balance between radiation and image quality are complex. This balance may be complicated by regional variations within different patients and by variations within each imaging volume which might otherwise be addressed by consideration of task-specific needs. For instance, an abdominal CT examination may feature a variety of tissues serving a variety of functions, however, as it relates to imaging, these varied tissues attenuate and scatter photons differently and must be considered differently, even within a same imaging volume. It can be appreciated that, in addition to already known differences between patients, imaging protocol optimization is not a trivial problem.

Moreover, a number of currently available imaging protocols are generalized to a broad population and, therefore, do not provide customized, patient-specific, and application-dependent functionality. Understanding that physicians routinely check medical image quality for various quality-related factors, such as artifacts, spatial resolution, contrast, and noise, it becomes more difficult to produce imaging protocols tuned for individual patients, diseases, and organs of interest while if clinician intervention is required at each step of optimization. Further, it is always desirable to scan the patient with a lower dose while keeping image quality at a clinically acceptable level. However, dose reduction leads to a lower signal-to-noise ratio (SNR) which can have consequences for the detectability of certain structures/pathologies. Automatic Exposure Control (AEC) seeks to optimize CT scan exposures automatically to reduce the radiation dose that the patient is exposed to, while keeping image quality consistent, simplifying the workflow for radiologists. Existing technologies can inaccurately determine the AEC which results in delivering inaccurate dose to the patient and/or sub-optimal image quality.

The foregoing "Background" description is for the purpose of generally presenting the context of the disclosure. Work of the inventors, to the extent it is described in this background section, as well as aspects of the description which may not otherwise qualify as prior art at the time of filing, are neither expressly nor impliedly admitted as prior art against the present disclosure.

SUMMARY

To provide an accurate dose and to avoid long radiation exposures of the patient during the CT scan, Automatic Exposure Control (AEC) for delivery of an appropriate radiation dose to the patient can be fine-tuned and the corresponding image quality can be more efficiently predicted for a given clinical task. Factors that result in sub-optimal image quality may include inaccurately determining the dose without taking into consideration that noise in certain types of tissues (e.g., in soft-tissue) may not be uniform in different regions of the body. Another factor may be inaccurately determining the dose without taking into consideration that some organs may receive more than the necessary radiation dose while others may receive a lower dose leading to poor image quality for the specific task. Yet another factor may include limited information available before the CT scan, such as patient size, location within the scanner, and anatomical targets of interest that prevent the use of patient-specific configurations.

Accordingly, the present disclosure describes a method, apparatus, and non-transitory computer-readable storage medium for image quality improvement based on noise and dose optimization during the determination of the AEC.

For each clinical task having an initial radiation dose (also referred to as an initial exposure) that is clinical task-specific, the method includes using a pre-scan to obtain at least one factor to be used to adjust the initial radiation dose using an AEC system and/or method. For example, one factor can be a location-specific amount of image noise either in general or in a particular type of tissue. Another factor can be the presence or absence of a sensitive organ in the exposure area. More than one factor can be combined to generate an adjusted factor-based exposure.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A complete appreciation of the disclosure and many of the attendant advantages thereof will be readily obtained as the same becomes better understood by reference to the following detailed description when considered in connection with the accompanying drawings, wherein:

FIG. 8 is a block diagram of a process of segmenting a reconstructed image into regions of at least one tissue to use as a mask when generating tissue specific noise data;

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The present disclosure describes a method for image quality improvement and/or reduced risk of patient exposure based on Automatic Exposure Control (AEC) in a main imaging scan (e.g., in computed tomography (CT) scan, in a tomosynthesis scan, and in a VCT (X-ray volume CT) scan) based on a spatially-distributed characteristic from the sinogram/projection data of a pre-scan/scout scan preceding the main CT scan. The spatially-distributed characteristic may include, but is not limited to, (1) a spatially-distributed noise characteristic of the pre-scan and/or (2) a spatially-distributed identification of exposure-sensitive tissue types.

Figure 1:
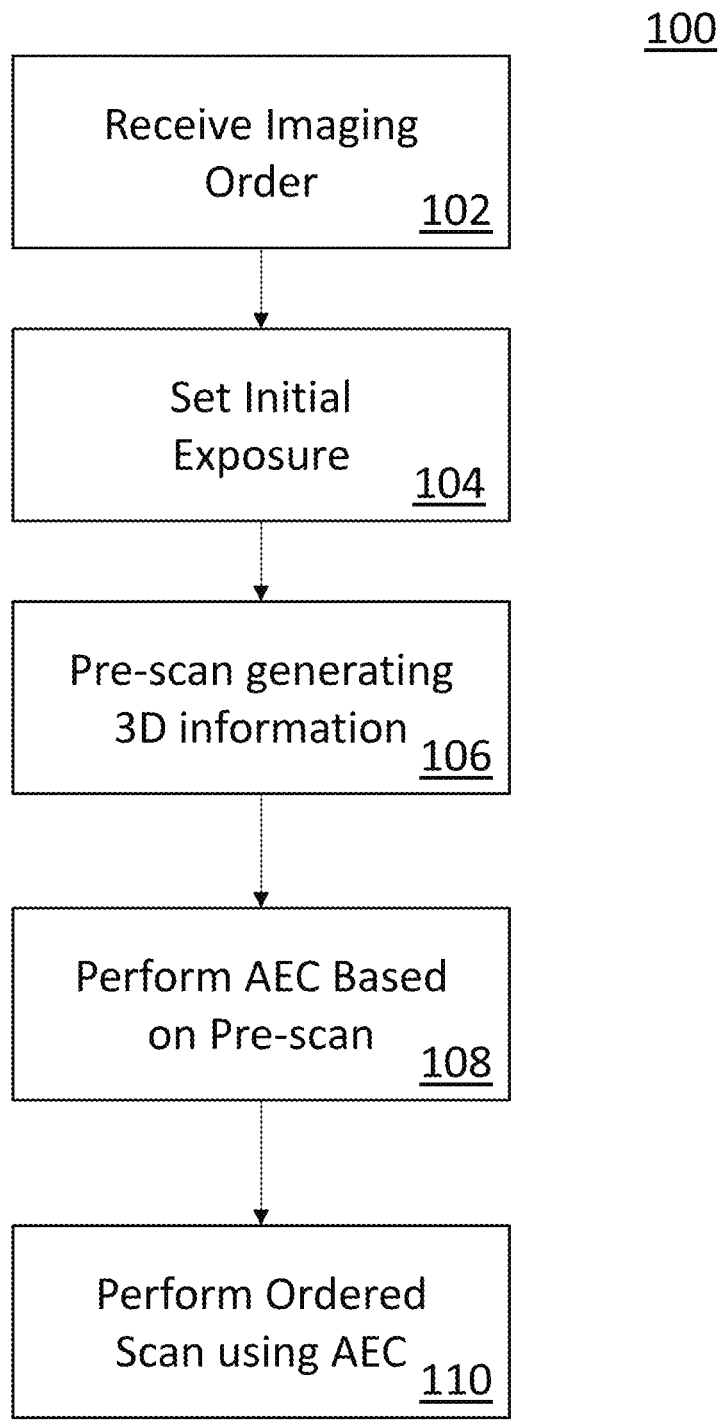
FIG. 1 is a flow diagram of a method for image quality improvement based on dose/exposure optimization as part of Automatic Exposure Control (AEC), according to an exemplary embodiment of the present disclosure.

Turning now to the Figures, FIG. 1 is a flow diagram of a method for image quality improvement based on AEC. The flow diagram of FIG. 1 describes method 100. At step 102, an imaging order is received for an imaging task that is to be performed (e.g., an imaging of the lungs). Based on the received imaging order, the processing circuitry for performing the method receives (e.g., from a database) or generates itself a curve representing an initial exposure/dose to be applied over the area to be imaged, and that curve is set as the initial exposure in step 104. This initial exposure may be constant for the entire area to be imaged or may vary depending on the received order. Generally, prior to submitting a patient to a full CT scan (i.e., full radiation dose), and in order, for example, to confirm positioning of the patient relative to the imaging area and/or a general size of the patient, known systems utilize a low-dose pre-scan (e.g., using only two orthogonal views) that provides limited detail about the patient. However, as part of the method 100, step 106 is performed by the system and generates a 3D pre-scan (also called a 3D scout scan) with a sufficient amount of detail to distinguish various internal tissues and/or spatially distributed characteristic information. The results of the 3D scout scan 106 are then used to modify the initial exposure as shown in step 108. Based on the modified dose, the scan that was ordered can be performed using AEC corrected exposure/radiation amounts (e.g., by varying an X-ray tube current amount) while the patient is still on the imaging table on which the 3D pre-scan was just performed. Thus, in a single examination the 3D pre-scan and the main scan are performed sequentially.

Figure 2:
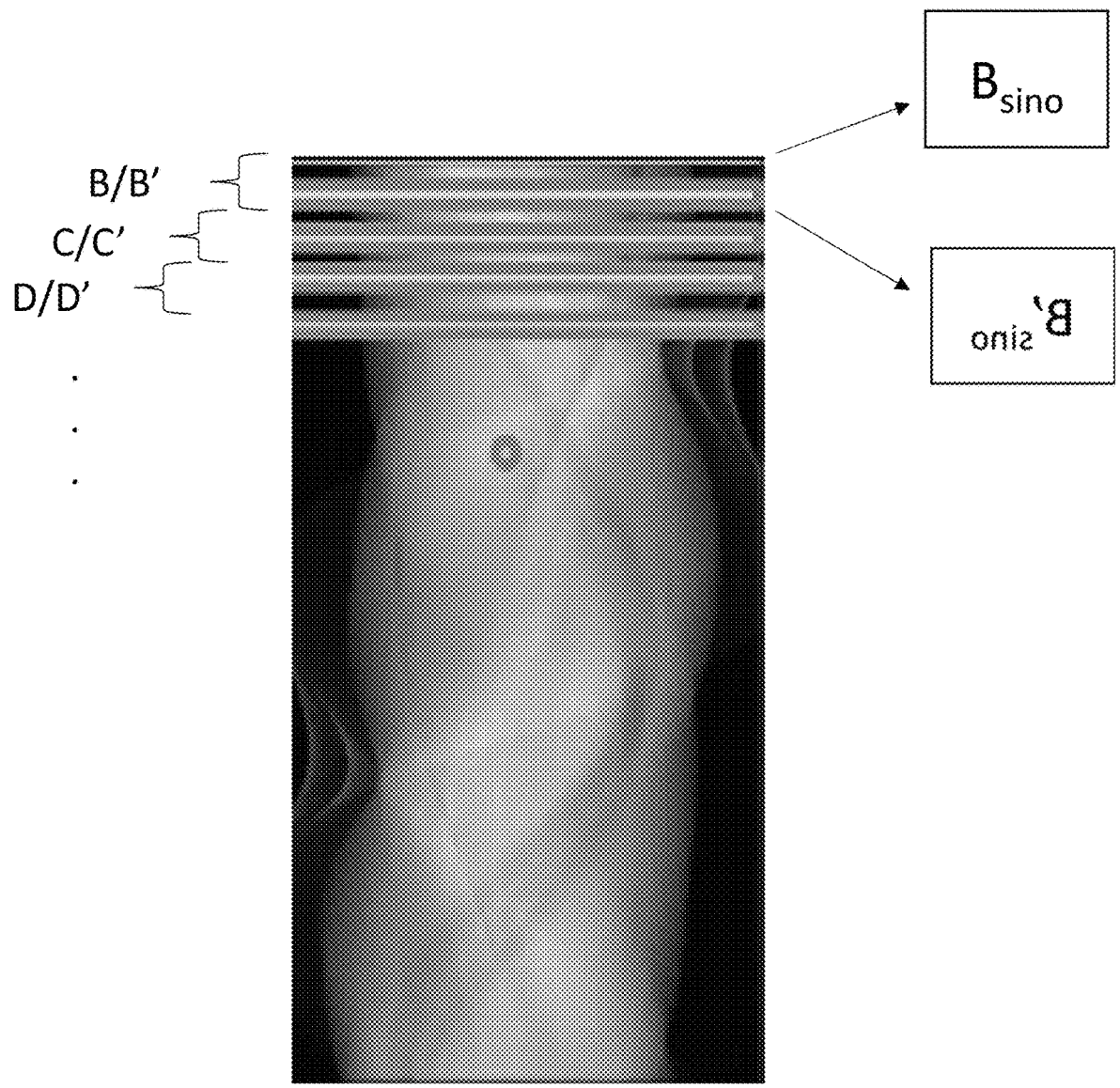
FIG. 2 is an illustration showing a set of sinogram data having been acquired as part of a pre-scan (scout scan) of FIG. 1 with the sinogram data being split into logical blocks of data that can be used to perform Automatic Exposure Control.
Figure 3:
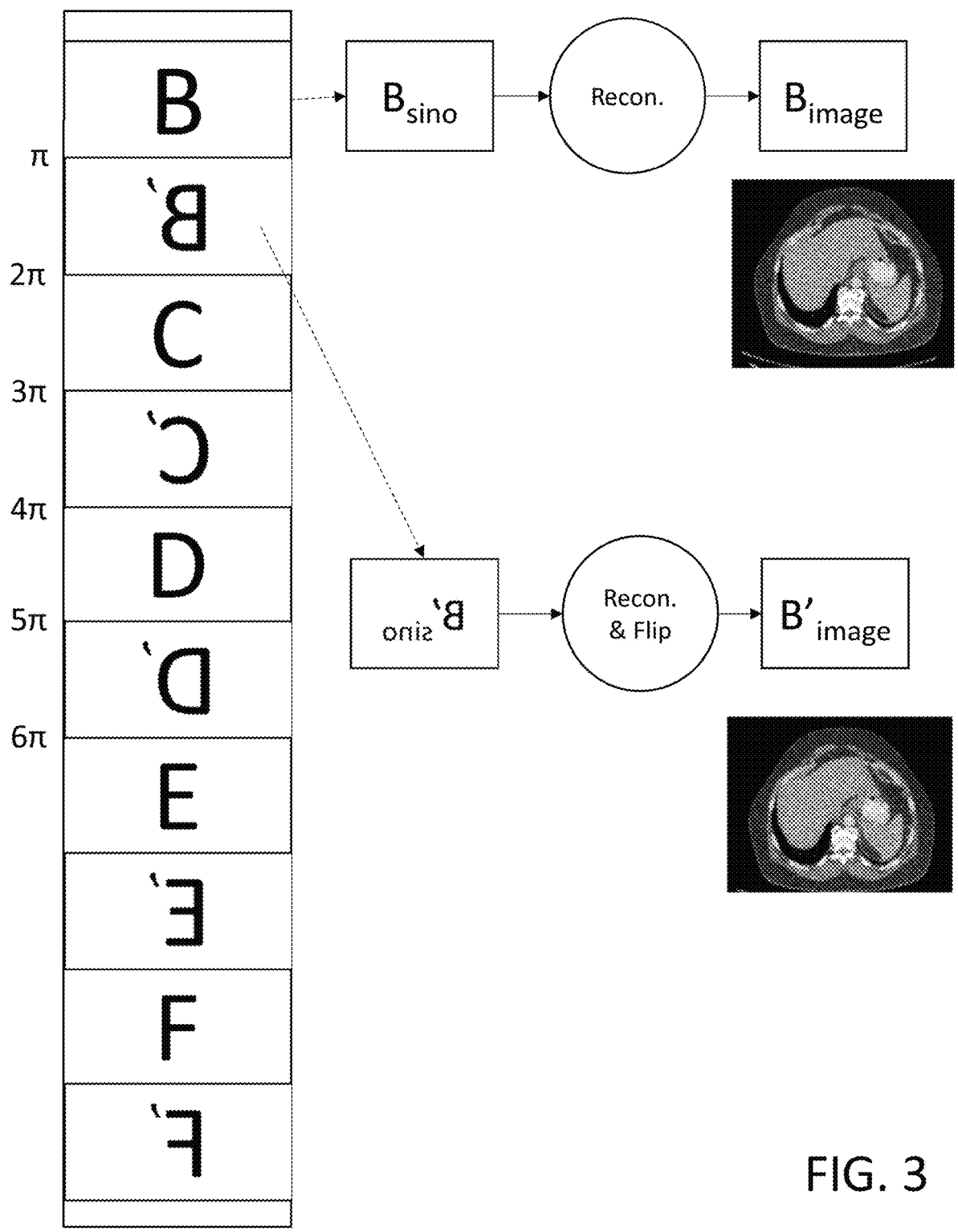
FIG. 3 is an illustration showing a series of blocks of FIG. 2 being reconstructed in half-scan reconstructions to produce two different slice images corresponding to a same location.

At noted above, in step 106 of method 100, a pre-scan operation is performed to obtain a set of sinogram data (also referred to as projection data) from a number of views corresponding to the pre-scanned area or region. As shown in FIG. 2, the pre-scan sinogram/projection data can be logically split into a series of blocks across the region having been imaged. FIG. 2 illustrates 4 sets of consecutive sinogram data (in bands) that are grouped to correspond to the subset of views that are within a same angular range. For example, the views obtained within the first π radians are considered to be the group B, and the views obtained within the second π radians is considered to be the group B' because they correspond to complementary views compared to the group B. As shown in FIG. 2, and as used in a number of subsequent figures, the views corresponding to group B' are sometime illustrated as being reversed compared to the group B to accentuate that the group B' corresponds to views taken from the opposite side compared to group B. However, as can be seen in FIG. 3, after a half-scan reconstruction, the resulting image of a slice from group B' can be flipped to be viewed in the same direction as a resulting slice from the half-scan reconstruction of group B for further processing. In such a configuration, one can assume illustrative views 1-16 in a set of views covering 2π radians could be split into two groups as (1) views 1-8 and (2) views 9-16. Alternatively, the groups B and B' can instead be set according to even and odd sets of views without departing from the scope of this disclosure. For example, 16 views could be split as (1) views 1, 3, 5, 7, 9, 11, 13, and 15 and (2) views 2, 4, 6, 8, 10, 12, 14, and 16. In general, the process of using sinogram data from all the different groups of views (illustrated as B-F' in FIG. 3) can produce a set of AEC corrections to provide improved image quality.

In another embodiment, any number of half scan projections may also be included, such that the half scan projections may be obtained randomly by choosing half of the projections from the full CT scan of the 3D scout sinogram reconstructed image, such that the half scan projections include non-overlapped data. For example, by randomly choosing one view from each consecutive set of two views and assigning it to a first group and assigning the other in the set to the second group, two exemplary groups could be (1) views 1, 10, 11, 4, 13, 6, 7, and 16 and (2) views 9, 2, 3, 12, 5, 14, 15, and 8. For some types of imaging processes, it may even be possible to allow a small number of views two overlap between the two groups. In one embodiment, "substantially non-overlapping" sets of views have at most 10% overlap between the views. In another embodiment, "nearly completely non-overlapping" sets of views have at most 5% overlap between views. As would be understood by those skilled in the art, although illustrated as separate groups of views that are processed separately and sequentially, the "groups" of views are really sliding windows of sinogram data that represent an amount of data needed to process (e.g., reconstruct) a view-specific noise correction factor at a location along the z direction corresponding to the scout scan.

Figure 14:
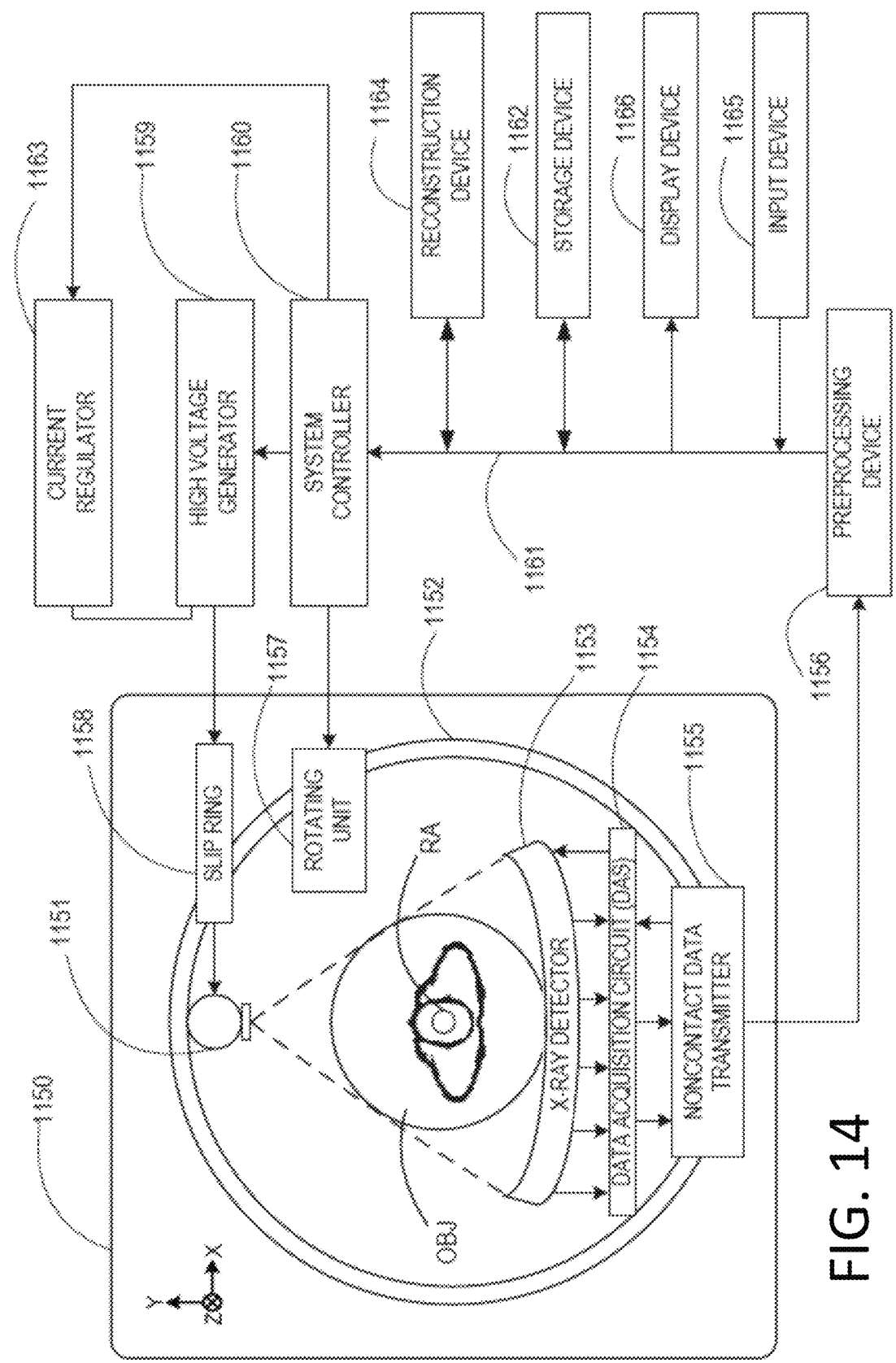
FIG. 14 is a schematic of an implementation of a CT scanner, according to an exemplary embodiment of the present disclosure.

At step 108 of method 100, in a first embodiment, AEC correction is calculated along the z axis (in the direction of the bore which is "into the page" of the system shown in FIG. 14) at locations corresponding to each of the views of the pre-scan. As used herein, the phrase "longitudinal direction" will refer to the "z" direction into the bore and which is "into the page" of the system shown in FIG. 14. In an alternate embodiment, fewer than all the views can be used to obtain the AEC corrections, and interpolation can be used between the calculated corrections. For example, to reduce processing time, a correction factor is calculated for every other view, and an average of the correction factors for the two adjacent views is used for the missing correction factor in between.

Figure 4:
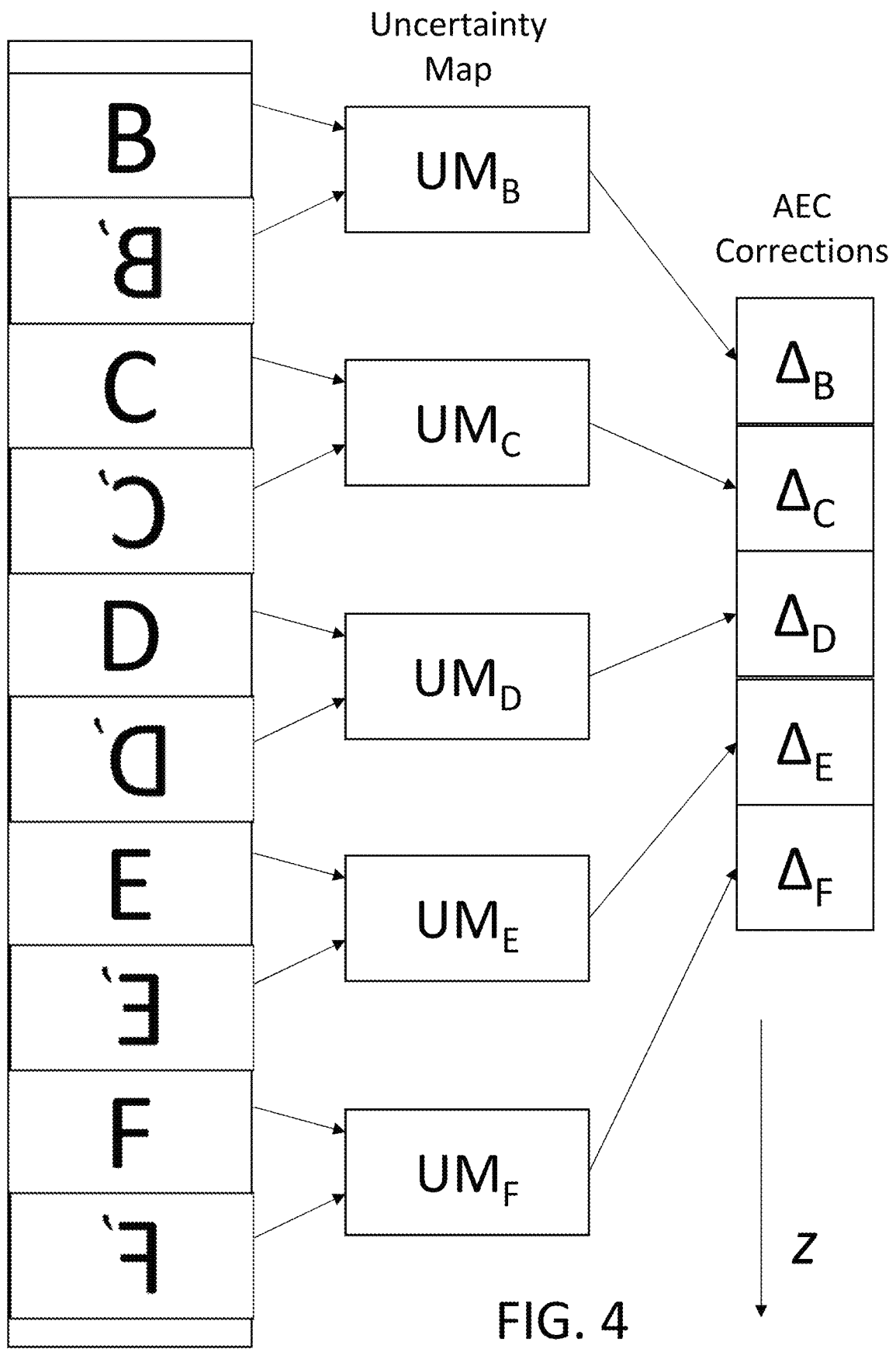
FIG. 4 is a data flow showing data a number of conversion steps for generating AEC corrections based on the pre-scan of FIG. 1.

As shown in FIG. 4, the sinogram data can be used to produce a view-specific uncertainty map based on the noise in the sinogram data, where the uncertainty map provides a spatial distribution of image noise in the imaged region that was scanned in three-dimensions. The uncertainty map then can be used to generate AEC corrections corresponding to the uncertainty map which varies in the longitudinal (z) direction.

Figure 5:
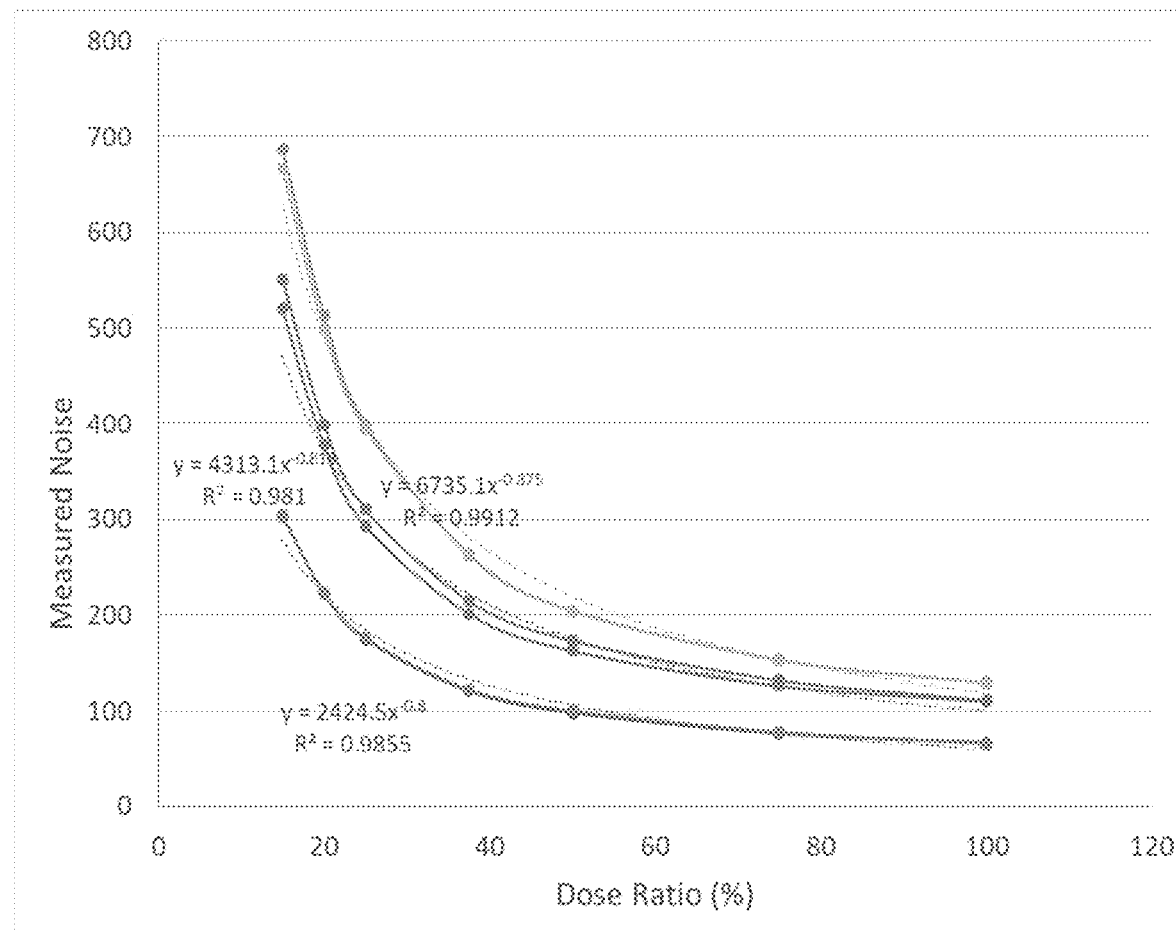
FIG. 5 is an illustration of a set of curves representing noise-based corrections to be applied as a part of an AEC correction of FIG. 1.

AEC Corrections can be obtained by reference to set of pre-calculated data correlating exposure correction to noise in a view. An exemplary series of curves is shown in FIG. 5. As shown in FIG. 5, an initial amount of exposure may be varied from 100% of the initial dose (i.e., no change on the right) to 0% (completely blocked on the left) depending on an amount of measured noise in a view. As illustrated in FIG. 5, a method may use more than one curve to handle different imaging conditions, as described in greater detail below.

Figure 6:
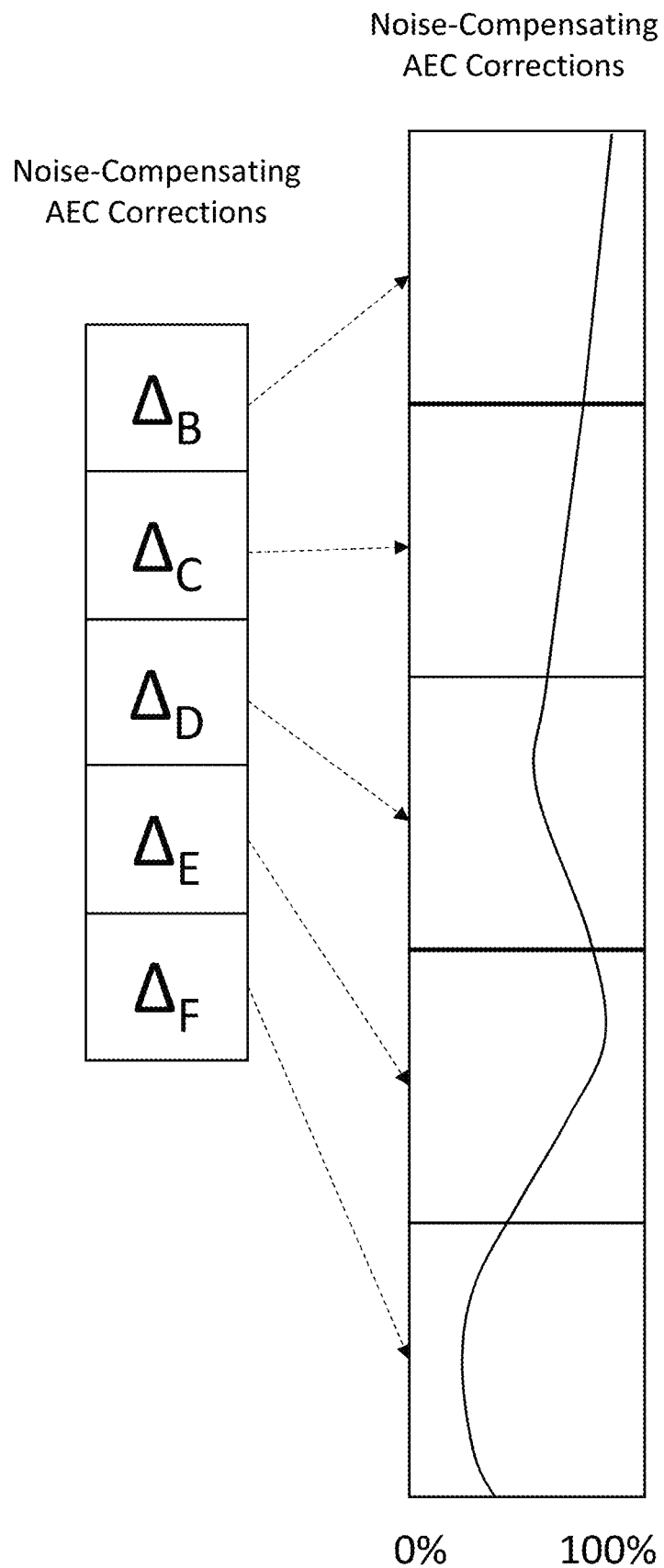
FIG. 6 is an illustration of exemplary curves of AEC corrections being generated based on the noise data calculated in FIG. 4.

FIG. 6 illustrates an exemplary graph (for illustrative purposes only) corresponding to the calculated noise-compensating AEC corrections that can be illustratively calculated with respect to FIGS. 4 and 5. As can be seen from the illustration, based on the spatial distribution of the noise calculated with respect to varying views across the pre-scan, an amount of exposure to be provided during a main scan can be varied (e.g., to keep noise at a particular level throughout the main scan).

Figure 7A:
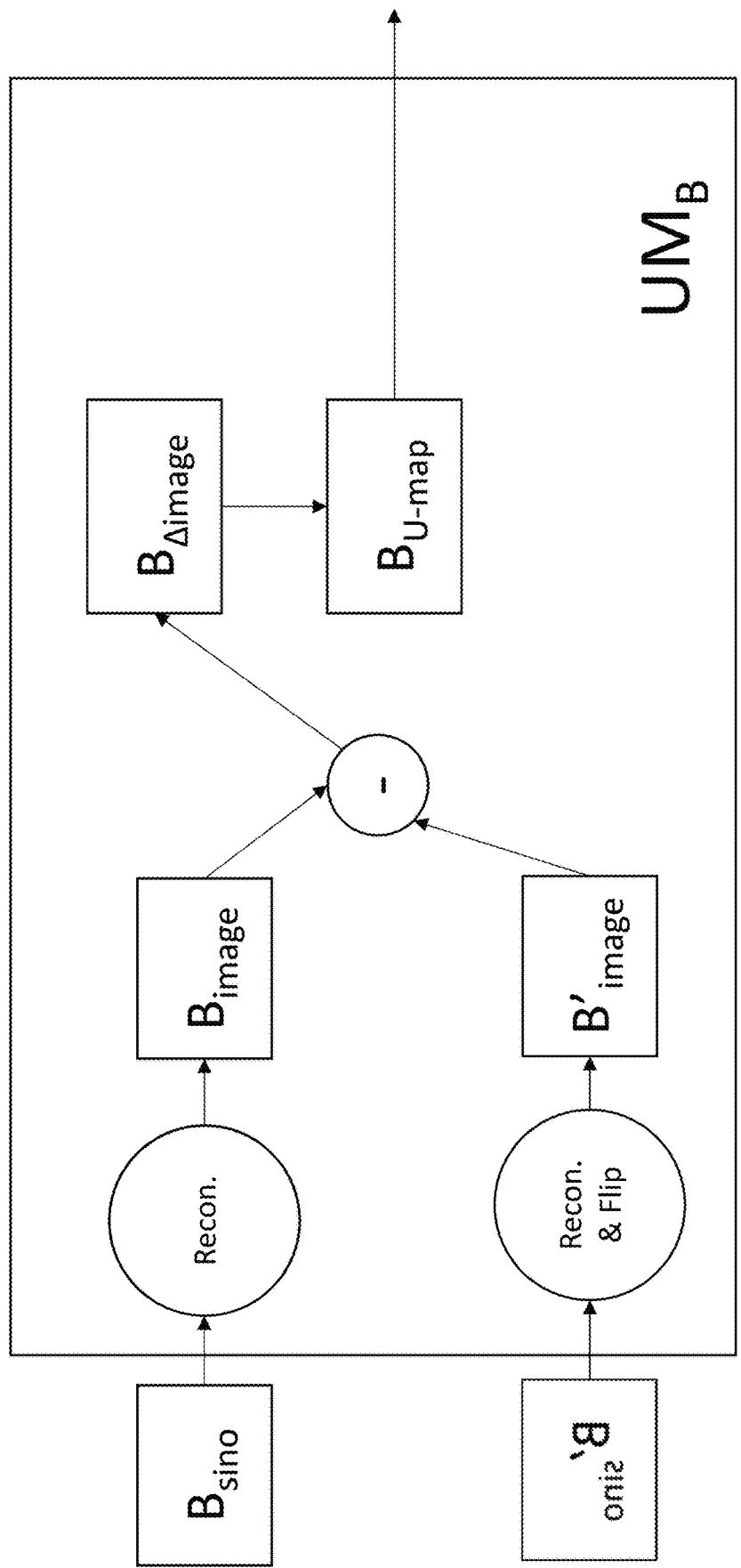
FIG. 7A is a block diagram of a first embodiment of a noise data calculation method as shown in FIG. 4 as part of the AEC correction calculation of FIG. 1 in which the noise data is calculated using reconstructed image data.

FIG. 7A is a block diagram of a first embodiment of a noise data calculation method (e.g., as performed by processing circuitry for carrying out the method) as shown in FIG. 4 as part of the AEC correction calculation of FIG. 1 in which the noise data is calculated using reconstructed image data. As illustrated therein, views from group B and views from group B' can be used to reconstruct images corresponding to the same slice using reconstruction for the views of group B and using a reconstruction and flip for the views from group B'. The two reconstructed images (labeled $B_{image}$, and $B'_{image}$) can then be subtracted (as represented by the "−" sign therebetween) (and potentially modified by a scalar, such as by dividing by two) to produce a difference image $B_{\Delta image}$. The difference image $B_{\Delta image}$ can then be converted to a noise heatmap which represents a distribution of noise within the reconstructed image. The heatmap for the view can then be converted to a scalar value (e.g., by summing the magnitude of heatmap values on a pixel-by-pixel basis across the heatmap) thereby representing the uncertainty at the location corresponding to the reconstructed image $B_{image}$. The uncertainties for all the views in the group B views can be grouped together to create an uncertainty map $B_{U\text{-}map}$ for the group B views. The uncertainty map $B_{U\text{-}map}$ can then be used with respect to a dose ratio curve (e.g., as shown in FIG. 5) to produce a spatially-distributed (in the z direction) set of noise-compensating AEC corrections.

Figure 7B:
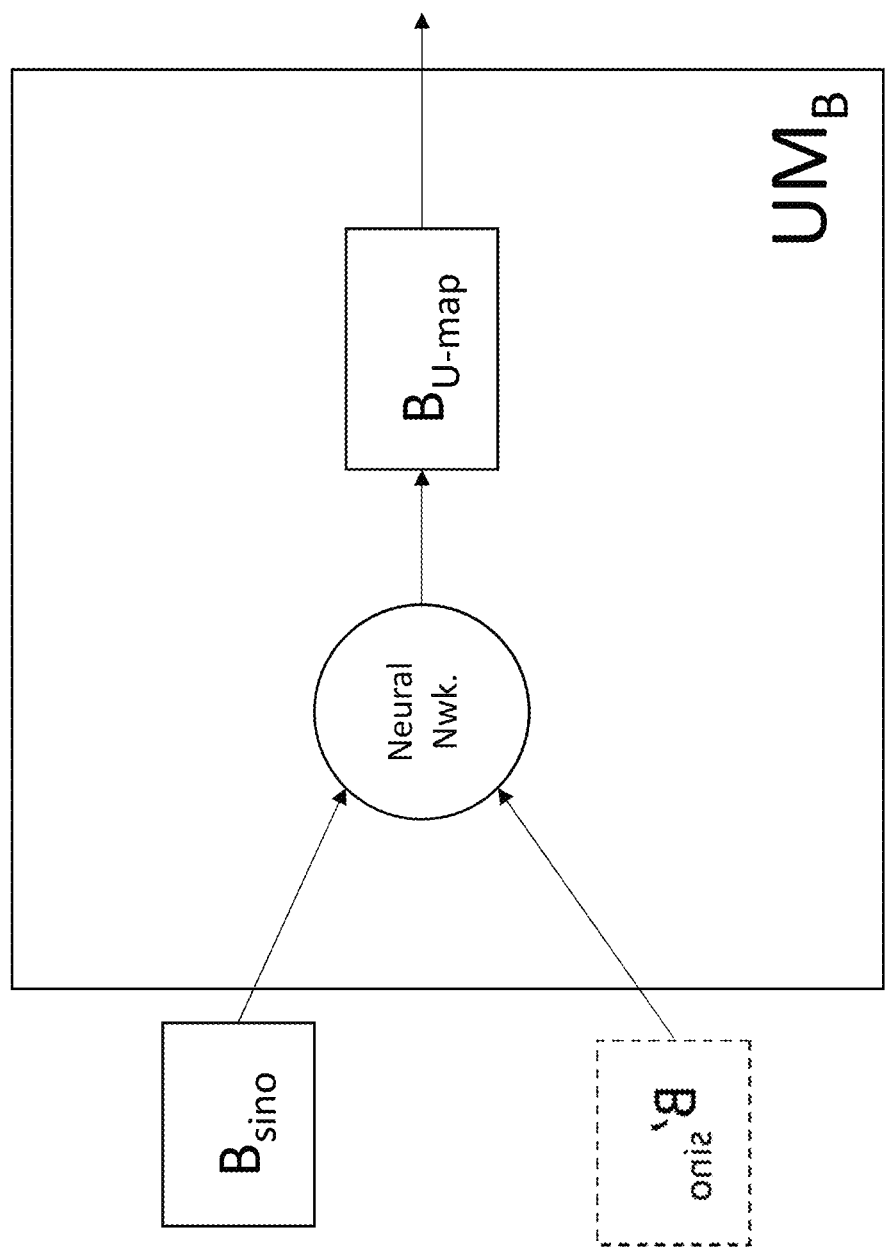
FIG. 7B is a block diagram of a second embodiment of a noise data calculation method as shown in FIG. 4 as part of the AEC correction calculation of FIG. 1 in which the noise data is calculated using sinogram image data fed to a neural network.

FIG. 7B is a block diagram of a second embodiment of a noise data calculation method as shown in FIG. 4 as part of the AEC correction calculation of FIG. 1 in which the noise data is calculated using sinogram image data fed to a neural network. As shown, the neural network can be applied to a number of different views. In a first embodiment, sinogram image data sufficient to perform a half scan reconstruction is used, but alternatively sinogram image data for a full scan reconstruction or for two half scan reconstructions can be used. In the second embodiment, rather than performing image reconstruction on the sinogram data, the sinogram data is processed directly using a trained neural network that generates an uncertainty map value from a set of sinogram data. By iteratively applying all the different sinogram data to the trained neural network, an uncertainty map can be generated across all the views of the corresponding group in the longitudinal direction. FIG. 7B shows the processing of sinogram data corresponding to the views of group B, but the process can be repeated (either serially or in parallel) for all other groups to produce the complete uncertainty map for the pre-scan.

In one embodiment of the system of FIG. 7B, the neural network is trained using uncertainty values obtained from a system as shown in FIG. 7A. That is, using training sinogram data as inputs (i.e., as a reference data set) and using as target values the uncertainty values obtained through the process described above with respect to the reconstructed images of FIG. 7A, a network can be trained to produce uncertainty map values directly from sinogram data, thereby avoiding the processing required to reconstruct slices from the sinogram data of the pre-scan.

Figure 7C:
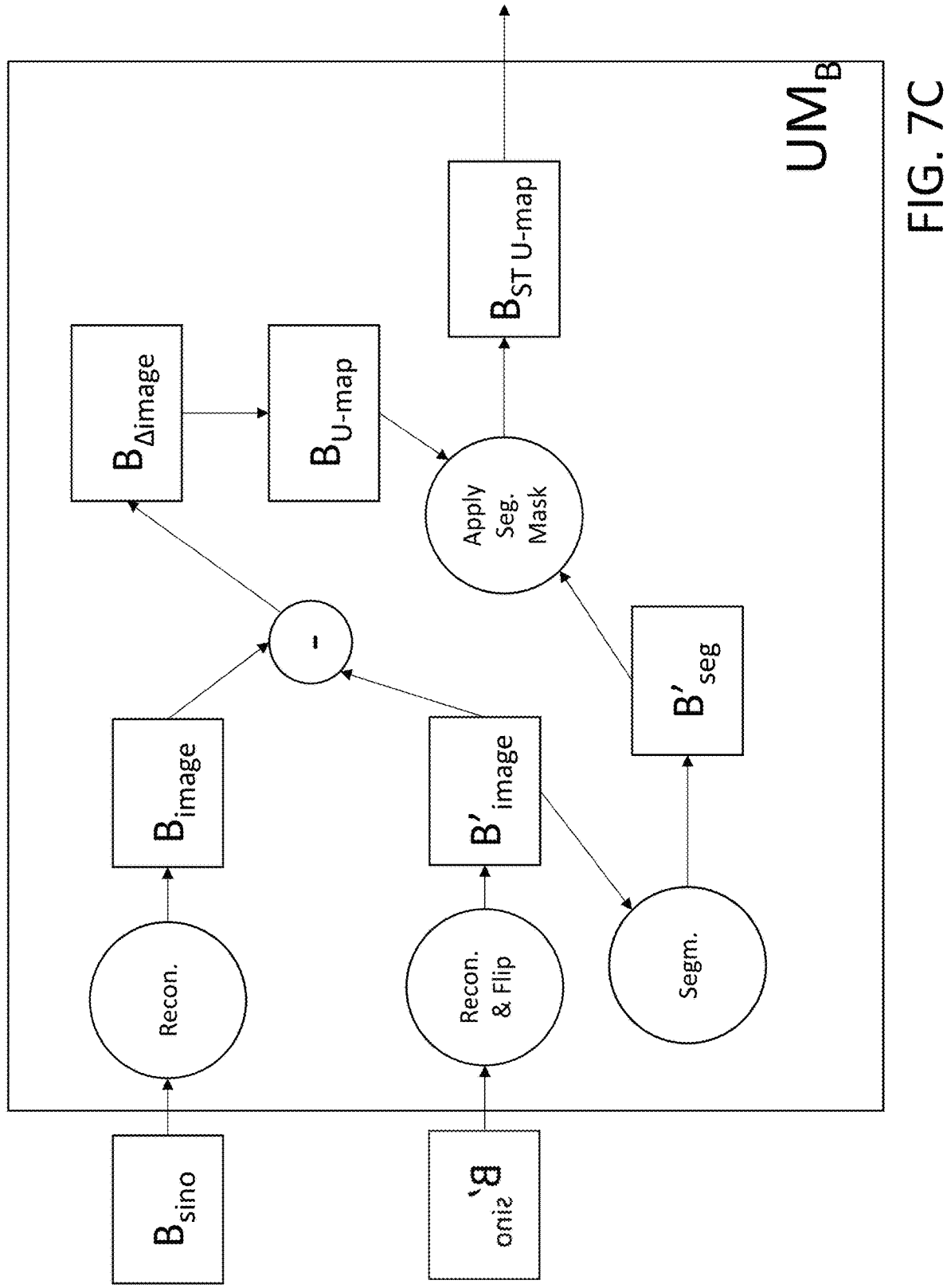
FIG. 7C is a block diagram of a third embodiment of a noise data calculation method as shown in FIG. 4 as part of the AEC correction calculation of FIG. 1 in which the noise data is calculated using reconstructed image data which has been segmented into tissue-specific areas.

FIG. 7C is a block diagram of a third embodiment of a noise data calculation method as shown in FIG. 4 as part of the AEC correction calculation of FIG. 1 in which the noise data is calculated using reconstructed image data which has been segmented into tissue-specific areas. Such a configuration is similar to the configuration of FIG. 7A but further adds image segmentation of at least one of $B_{image}$, and $B'_{image}$. As would be appreciated by one of skill in the art, although image $B'_{image}$ is illustrated as being segmented, $B_{image}$ could instead be segmented without departing from the teachings of this disclosure. As shown in FIG. 7C, image segmentation is performed to produce a segmented image $B'_{seg}$. Segmentation techniques include, but are not limited to, HU-based thresholding which operates to segment out the soft-tissue region based on HU value range, to get rid of other anatomical tissues, such as bone, air, etc. In addition, as noted herein, other segmentation methods also are possible.

FIG. 8 is a block diagram of a process of segmenting a reconstructed image 800 into regions of at least one tissue to use as a mask when generating tissue specific noise data. The segmented image $B'_{seg}$ corresponds to a map of the pixels of the image and what tissue type the pixel belongs to. For example, a reconstructed image shown in FIG. 8 can undergo image processing to detect various tissue types and "air" indicating that no tissue is present. As illustrated in the segmented image 805, at least three types of tissue have been identified: soft tissue=$T_{ST}$, lung tissue=$T_L$ and bone=$T_B$. However, other types of tissue (e.g., fat) can be identified as well including other organ types, such as breast, eyes, reproductive organs, kidney, heart, liver, pancreas, and stomach. Depending on the type of tissue whose noise is to be isolated, the segmented image is then applied as a mask to the corresponding portions of the noise heatmap 810 to produce a tissue-specific heatmap 815. As can be seen in the tissue-specific heatmap 815, only the noise corresponding to the soft tissue remains when a soft-tissue specific noise correction is to be determined. The remaining noise (e.g., $N_{12}, N_{13} \ldots$) can then be aggregated (e.g., by summing their magnitudes) to produce the corresponding scalar value for the reconstructed image 800 to be added to the soft tissue-specific uncertainty map (shown in FIG. 7C as $B_{ST\ U\text{-}map}$).

This uncertainty map then is used to make AEC corrections as described above which result in keeping the noise level of soft tissue the same across the main scan. As would be appreciated by those of skill in the art, other types of tissue could instead be targeted to make the noise across that tissue the same instead.

In addition to, or instead of the noise-based corrections described above, the pre-scan 106 can be used to generate organ-specific corrections that can be independently controlled as compared to the noise level that is to be targeted in the final scan. In a first embodiment, the organ-specific correction information is independent of the patient to be imaged. In such a configuration, the presence (or absence) of a particular organ in a particular location is all that is needed to control the exposure adjustment. For example, exposure levels in the presence of breasts, eyes, and reproductive organs are each assigned different correction factors that attempt to reduce their exposures. Other organs (e.g., liver and kidney) may be at yet different correction levels that allow greater exposure than the more sensitive areas.

In a second embodiment, patient-specific organ-specific corrections can be used. In such an embodiment, patient-specific information (e.g., a disease state of an organ and/or a previous amount of radiation exposure to an organ) may be entered, either manually by a user interface or automatically by automatically cross-referencing patient information relating to previous visits/treatments (e.g., by querying a local or remote medical record system including a database of records relating to the patient). Other patient information (e.g., patient age, sex, race, weight, and/or height) also may be entered either manually or by executing a query. Such information can further control the organ-specific corrections described herein.

Figure 9:
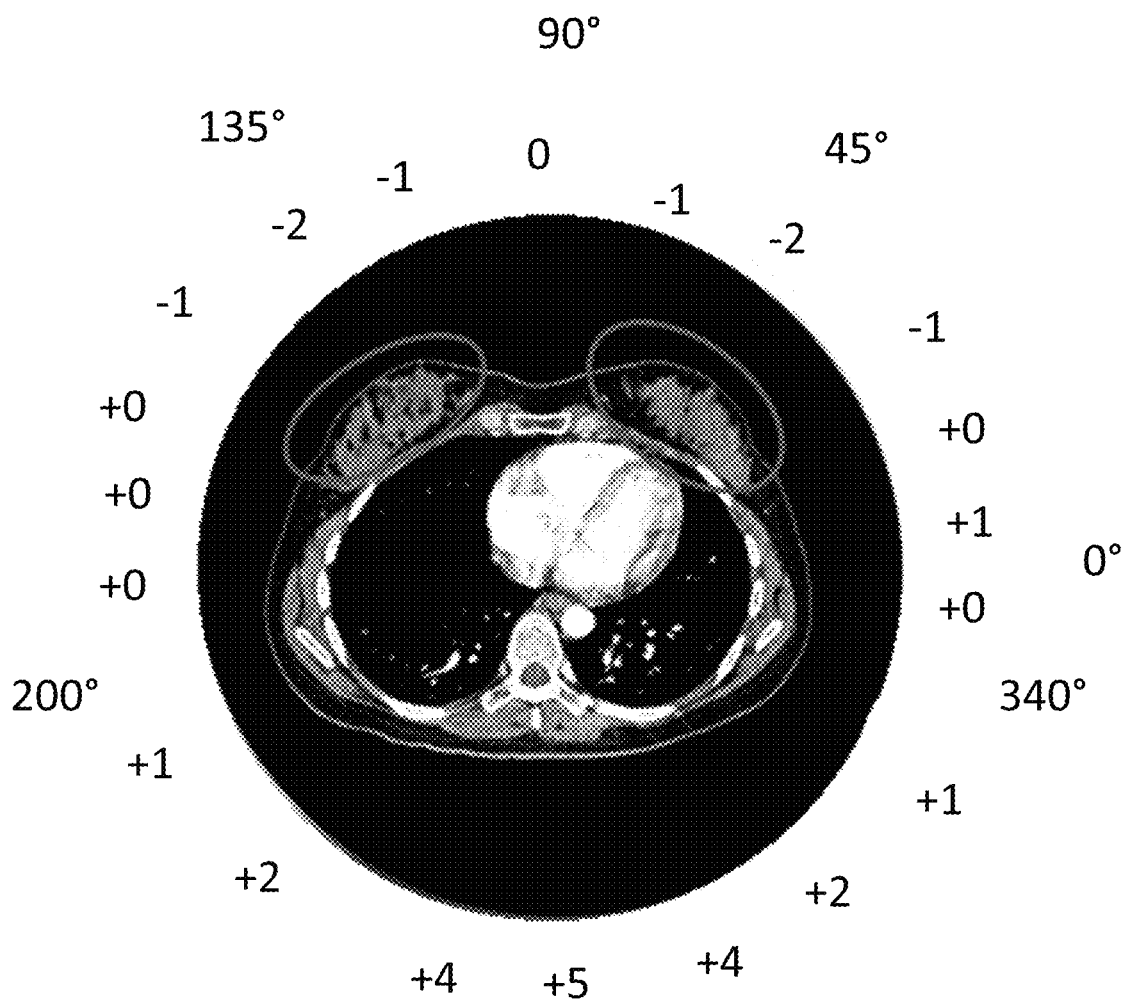
FIG. 9 is an illustration of an organ oriented mask, according to an exemplary embodiment of the present disclosure.

As shown in FIG. 9, the processing circuitry can determine from a reconstructed image the organs within the reconstructed image. As one or more organs may be sensitive to exposure from radiation, the processing circuitry may create an organ map that corresponds to changes to be made to an initial radiation dose so as to reduce overexpose of any sensitive organs where possible. The organ map is shown on an outside of a reconstructed image for the purposes of illustration, but the organ map is intended to be used on a view-by-view basis based on an angle at which the view is obtained. The processing circuitry thereby creates a spatially-distributed and rotationally-specific organ sensitivity characteristic spatially distributed in the longitudinal direction and varying depending on an angle of an x-ray transmitter. For example, the organ map indicates that for the current slice the organs (e.g., breast tissue) that are most sensitive (−2) are at angles 45 degrees and 135 degrees. The sensitivity decreases (to a 0 correction factor) at a number of angles (e.g., near 180 degrees). As illustrated, the organ map also can take into consideration the presence of the table on which the patient is being imaged. For example, starting at around 200 degrees, the sensitivity is decreased so that radiation can increase to compensate for the presence of the table. For illustrative purposes, the organ map has a greatest correction when the x-ray transmitter is below the table at about 270 degrees. As can be seen from FIG. 9, the organ map need not be symmetrical. Also, as would be understood by those of skill in the art, the organ map would have contained different values had the patient been face down on the table such that a portion of the corrections for the breast tissue would have been offset by the presence of the table. The corrections described herein can be combined in a number of ways that may be organ specific, but at least some correction combination techniques include (but are not limited to): linear combinations of corrections, weighted combinations of corrections, and combinations of corrections both with and without thresholds. For example, if the radiation level is already below a particular level, exposure is not adjusted at a "sensitive" organ to ensure image quality. In yet another embodiment, the medical professional is warned that the exposure level cannot be sufficiently reduced using the automatic correction and asks for an override or recommends not administering the imaging.

In an embodiment performing only the organ-specific corrections, the pre-scan may be performed in a different examination than the main scan and the organ map stored for later use. In such a configuration, registration of a patient's current and previous positions are performed using a marker on the patient or external images of the patient using a camera. Alternatively, the patient may be aligned to markers on the imaging table.

Figure 10:
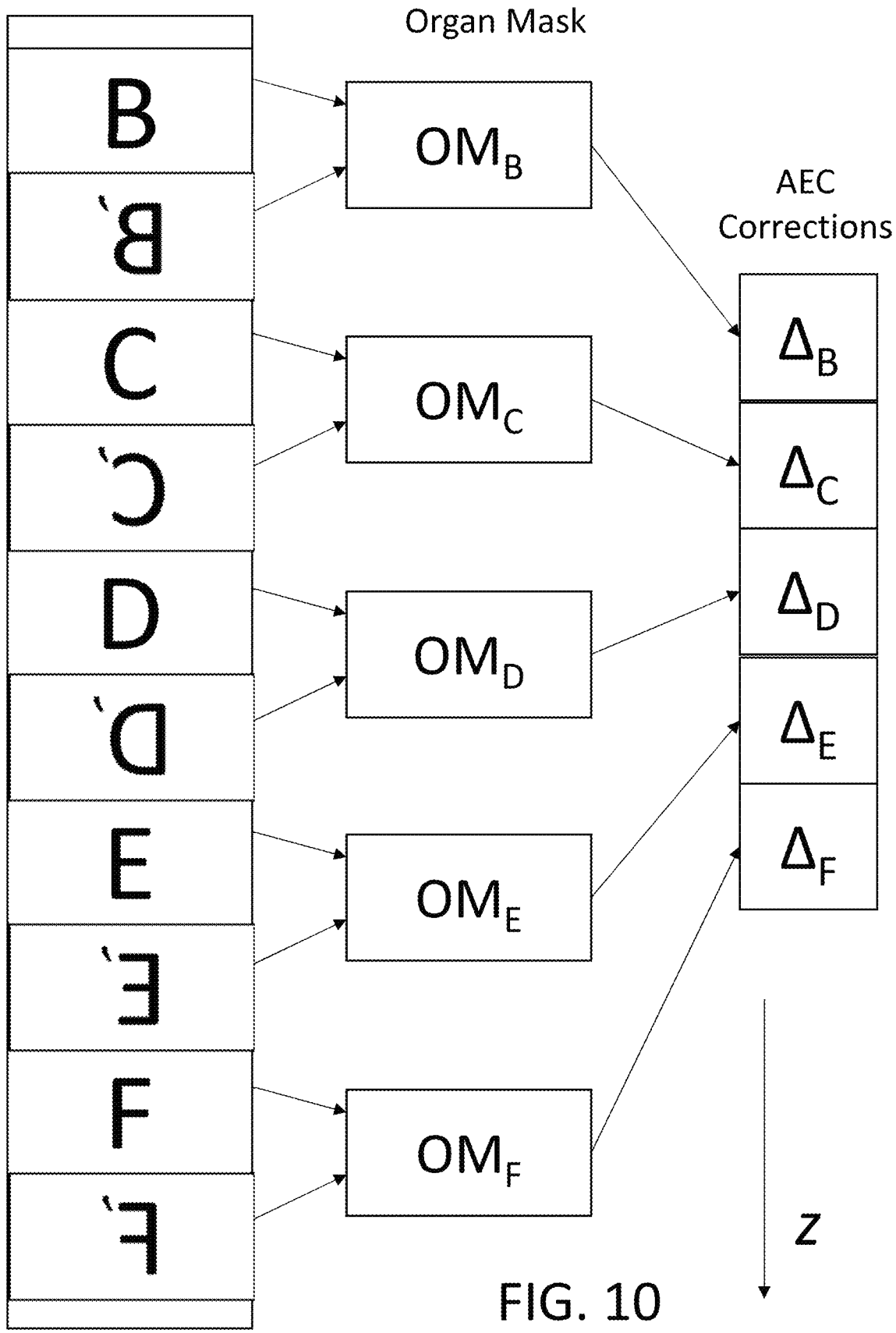
FIG. 10 is a block diagram showing generating an Organ Mask based on blocks of sinogram data acquired in the pre-scan of FIG. 1.
Figure 11:
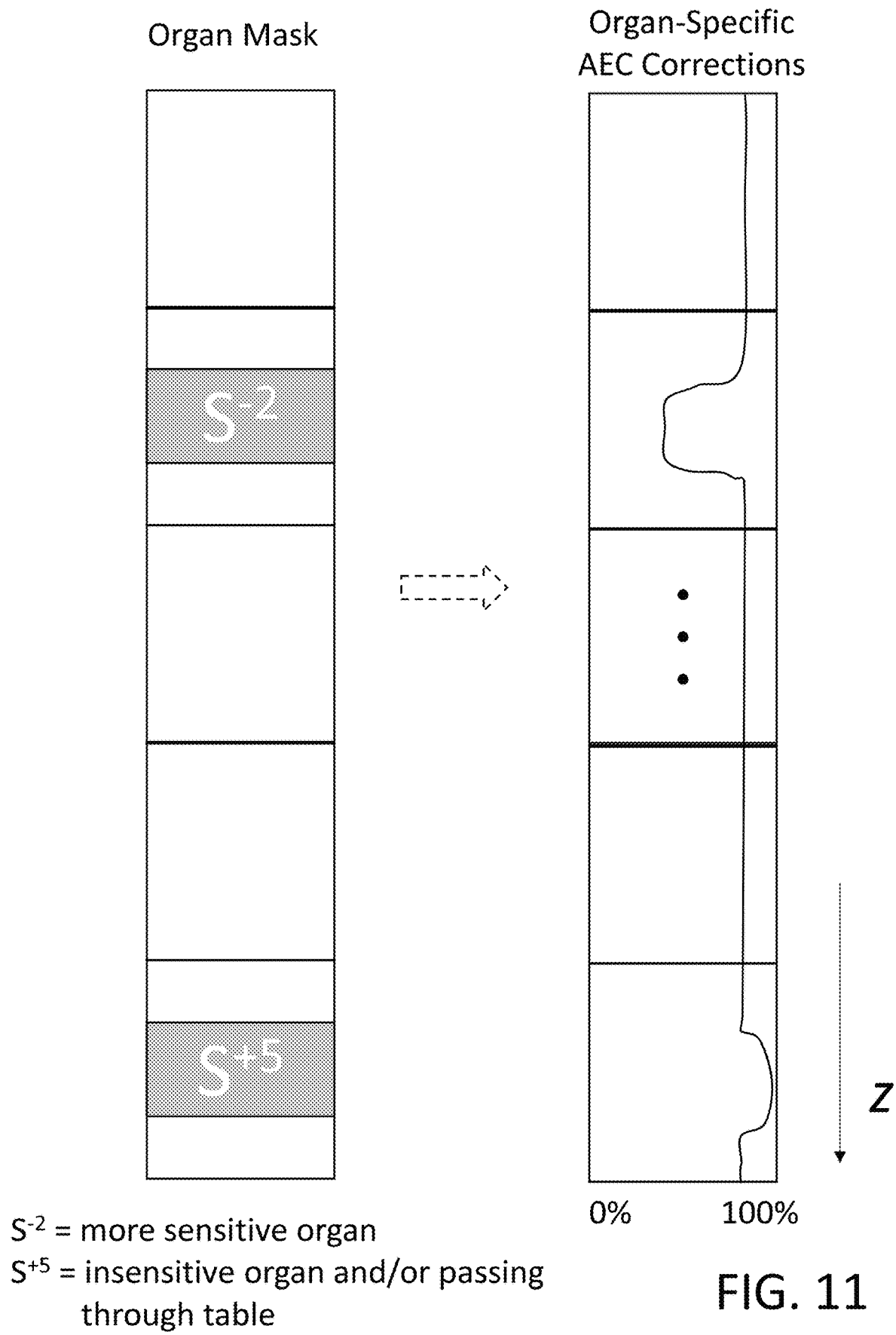
FIG. 11 is a block diagram showing conversions of an organ mask to organ-specific AEC corrections.

Similar to the noise corrections of FIG. 4, FIG. 10 shows a block diagram showing generating AEC corrections but based on Organ Mask based on blocks of sinogram data acquired in the pre-scan of FIG. 1. FIG. 11 also illustrates a block diagram showing conversions of an organ mask to organ-specific AEC corrections in a graph-based form. As illustrated therein, an original constant dose is corrected to decrease a dose in the presence of a sensitive organ (in a region identified as $S^{-2}$, such as would occur in a breast region corresponding to a "−2" designation in FIG. 9) and to increase a dose in the presence of an insensitive organ and/or the table (in a region identified as $S^{+5}$, such as would occur in a region corresponding to a "+5" designation in FIG. 9). As illustrated, a dose decrease corresponding to "−2" is more than a dose increase corresponding to "+5" for illustrative purposes. However, the positive and negative scales need not be identical or even proportional.

Figure 12A:
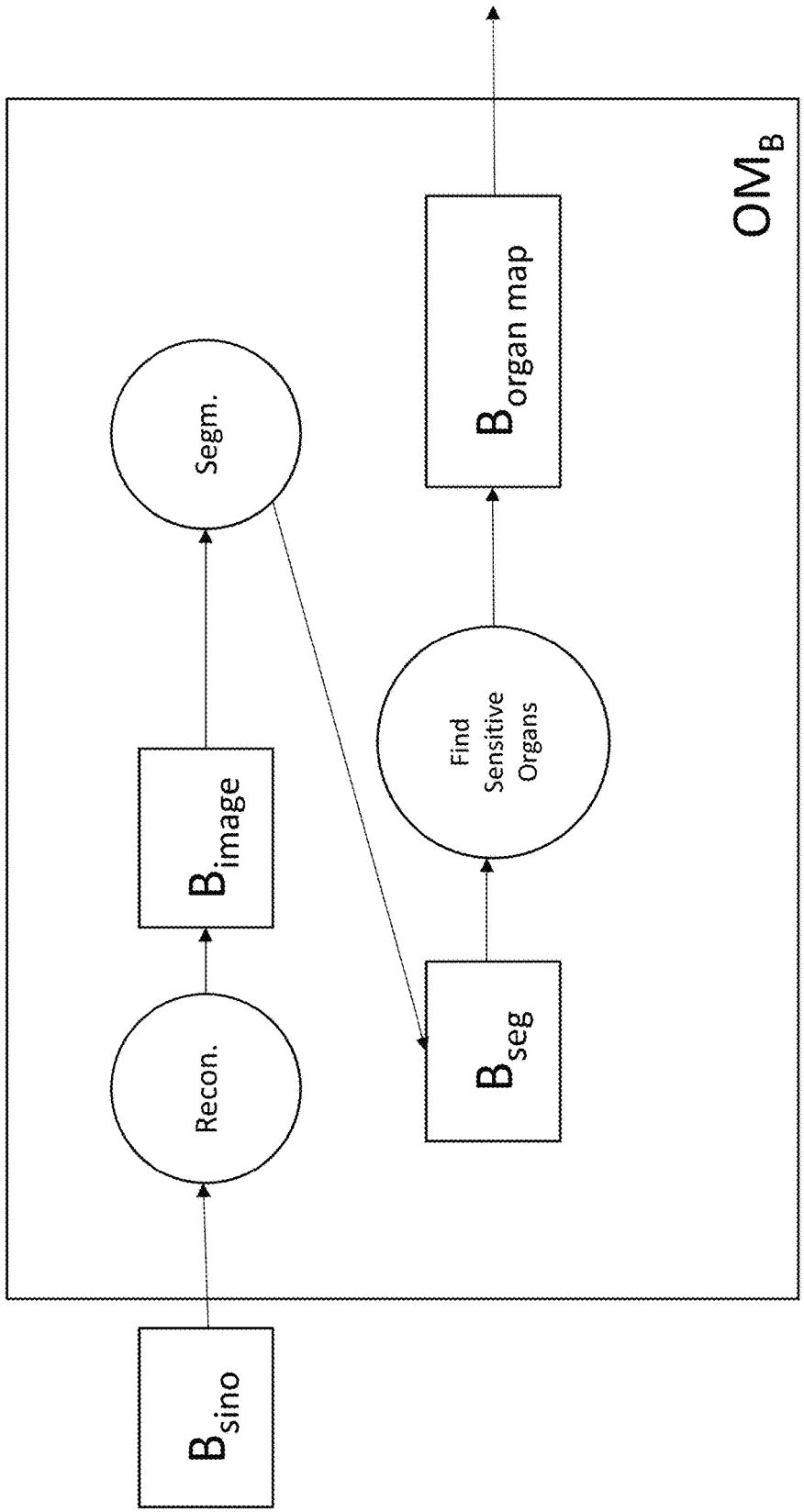
FIG. 12A is a block diagram illustrating a first embodiment for generating an organ map to be used to perform organ-specific AEC corrections.
Figure 12B:
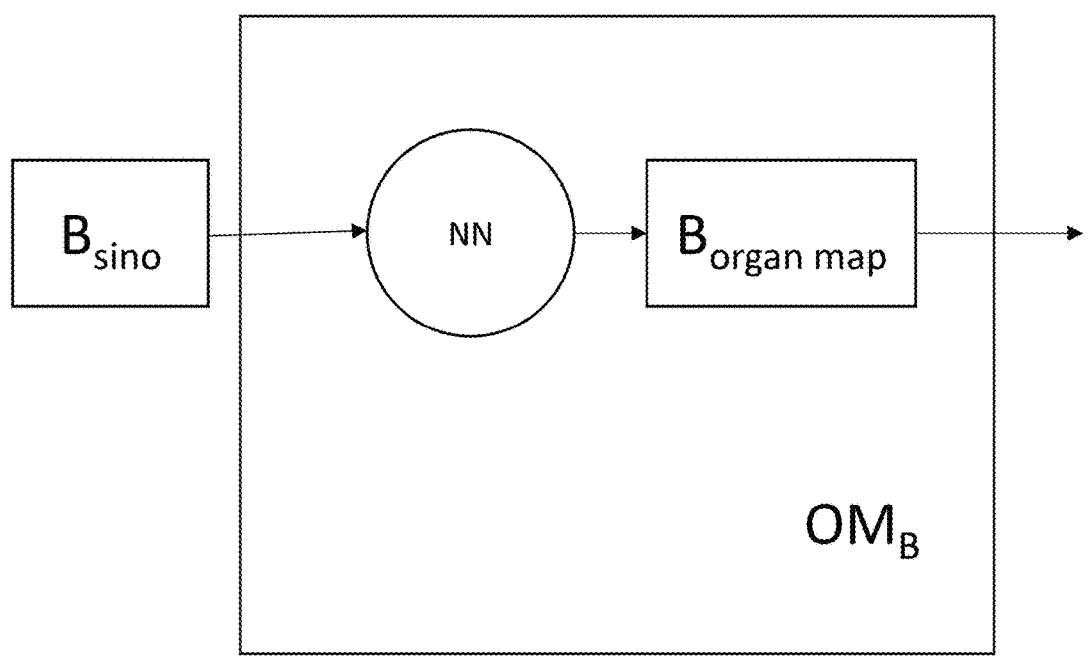
FIG. 12B is a block diagram illustrating a second embodiment for generating an organ map to be used to perform organ-specific AEC corrections.

FIG. 12A and FIG. 12B illustrate processes of generating an organ map according to first and second embodiments, respectively. In the first embodiment of FIG. 12A, at least one image is reconstructed from views in the B/B' group of views. The reconstruction can be a half-scan or a full-scan reconstruction. The reconstructed image $B_{image}$ undergoes a segmentation process to generate a segmented image $B_{seg}$ as was discussed above with respect to FIG. 7C. The various organs within the segmented image $B_{seg}$ can then be identified, for example, using pattern matching techniques and/or region growing techniques and optionally using information about identified organ in earlier portions of the organ identifying process. For example, the presence of an organ (e.g., the liver) in a reconstructed image of an adjacent view increases the likelihood that the current view will have one as well, and in a co-located position. In one embodiment, organ identification is performed as part of a network-based organ segmentation that uses HU-based thresholding.

Alternatively, as shown in FIG. 12B, a neural network can be used instead of the pattern matching/region growing techniques. In the second embodiment of FIG. 12B, rather than performing image reconstruction on the sinogram data, the sinogram data is processed directly using a trained neural network that generates an organ map value from a set of sinogram data. By iterating through all the different sinogram data, an organ map can be generated across all the views of the corresponding group. FIG. 12B shows the processing of sinogram data corresponding to the views of group B, but the process can be repeated (serially or in parallel) for all other groups to produce the complete organ map for the pre-scan in the longitudinal direction.

In one embodiment of the system of FIG. 12B, the neural network is trained using organ map values obtained from a system as shown in FIG. 12A. That is, using training sinogram data as inputs and using as target values the organ map values obtained through the process described above with respect to the reconstructed images of FIG. 12A, a neural network can be trained to produce organ map values directly from sinogram data, thereby avoiding the processing required to reconstruct slices from the sinogram data of the pre-scan.

Figure 13:
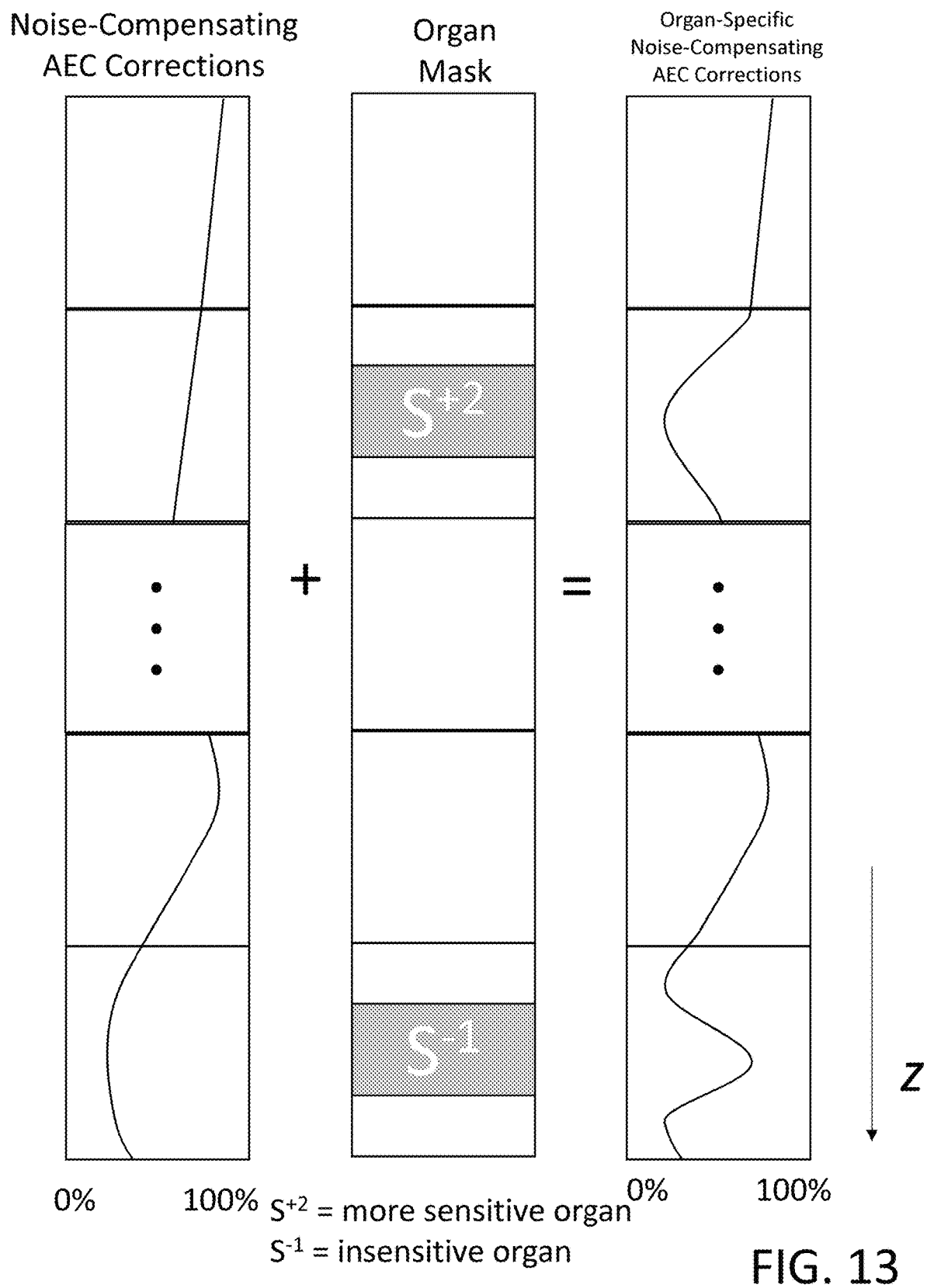
FIG. 13 is an illustration showing a process of applying an organ mask to noise-compensating AEC corrections to produce organ-specific noise-compensating AEC corrections.

The techniques described above of creating uncertainty maps and organ maps can be combined rather than used separately. For example, as shown in FIG. 13, a set of noise-compensating AEC Corrections further can be corrected by applying an organ mask so that a set of organ-specific noise-compensating AEC corrections can be produced.

According to an embodiment of the present disclosure, the above-described methods for patient-specific imaging protocols can be implemented as applied to data from a CT apparatus or scanner. FIG. 14 illustrates an implementation of a radiography gantry included in a CT apparatus or scanner. As shown in FIG. 14, a radiography gantry 750 is illustrated from a side view and further includes an X-ray tube 751, an annular frame 752, and a multi-row or two-dimensional-array-type X-ray detector 753. The X-ray tube 751 and X-ray detector 753 are diametrically mounted across an object OBJ on the annular frame 752, which is rotatably supported around a rotation axis RA. A rotating unit 757 rotates the annular frame 752 at a high speed, such as 0.4 sec/rotation, while the object OBJ is being moved along the axis RA into or out of the illustrated page.

An embodiment of an X-ray CT apparatus according to the present disclosures will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosures can be applied to either type. In this case, the rotate/rotate-type, which is currently the mainstream, will be exemplified.

The multi-slice X-ray CT apparatus further includes a high voltage generator 759 that generates a tube voltage applied to the X-ray tube 751 through a slip ring 758 so that the X-ray tube 751 generates X-rays. The X-rays are emitted towards the object OBJ, whose cross-sectional area is represented by a circle. For example, the X-ray tube 751 having an average X-ray energy during a first scan that is less than an average X-ray energy during a second scan. Thus, two or more scans can be obtained corresponding to different X-ray energies. The X-ray detector 753 is located at an opposite side from the X-ray tube 751 across the object OBJ for detecting the emitted X-rays that have transmitted through the object OBJ. The X-ray detector 753 further includes individual detector elements or units and may be a photon-counting detector. In the fourth-generation geometry system, the X-ray detector 753 may be one of a plurality of detectors arranged around the object OBJ in a 360° arrangement.

The CT apparatus further includes other devices for processing the detected signals from the X-ray detector 753. A data acquisition circuit or a Data Acquisition System (DAS) 754 converts a signal output from the X-ray detector 753 for each channel into a voltage signal, amplifies the signal, and further converts the signal into a digital signal.

The X-ray detector 753 and the DAS 754 are configured to handle a predetermined total number of projections per rotation (TPPR).

The above-described data is sent to a preprocessing device 756, which is housed in a console outside the radiography gantry 750 through a non-contact data transmitter 755. The preprocessing device 756 performs certain corrections, such as sensitivity correction, on the raw data. A memory 762 stores the resultant data, which is also called projection data at a stage immediately before reconstruction processing. The memory 762 is connected to a system controller 760 through a data/control bus 761, together with a reconstruction device 764, input device 765, and display 766. The system controller 760 controls a current regulator 763 that limits the current to a level sufficient for driving the CT system. In an embodiment, the system controller 760 implements optimized scan acquisition parameters.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 751 and the X-ray detector 753 are diametrically mounted on the annular frame 752 and are rotated around the object OBJ as the annular frame 752 is rotated about the rotation axis RA. In the fourth-generation geometry system, the detectors are fixedly placed around the patient and an X-ray tube rotates around the patient. In an alternative embodiment, the radiography gantry 750 has multiple detectors arranged on the annular frame 752, which is supported by a C-arm and a stand.

The memory 762 can store the measurement value representative of the irradiance of the X-rays at the X-ray detector unit 753. Further, the memory 762 can store a dedicated program for executing the CT image reconstruction, material decomposition, and PQR estimation methods including methods described herein.

The reconstruction device 764 can execute the above-referenced methods, described herein. The reconstruction device 764 may implement reconstruction according to one or more optimized image reconstruction parameters. Further, reconstruction device 764 can execute pre-reconstruction processing image processing such as volume rendering processing and image difference processing as needed.

The pre-reconstruction processing of the projection data performed by the preprocessing device 756 can include correcting for detector calibrations, detector nonlinearities, and polar effects, for example.

Post-reconstruction processing performed by the reconstruction device 764 can include generating a filter and smoothing the image, volume rendering processing, and image difference processing, as needed. The image reconstruction process may implement the optimal image reconstruction parameters derived above. The image reconstruction process can be performed using filtered back projection, iterative image reconstruction methods, or stochastic image reconstruction methods.

The reconstruction device 764 can use the memory to store, e.g., projection data, forward projection training data, training images, uncorrected images, calibration data and parameters, and computer programs. The reconstruction device 764 may also include processing support for machine learning, including calculating a reference data set based on the obtained spatial distribution in the soft tissue region and generating a filter by performing all or a portion of the machine learning process with the projection data set as input data and the reference data set as teacher data. Application of the machine learning, which may include application of an artificial neural network, also allows for the generation of one or more assessment values that are representative of the image quality.

The reconstruction device 764 may be implemented by one processor individually or in a network or cloud configuration of processors. The reconstruction device 764 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 762 can be non-volatile, such as ROM, EPROM, EEPROM or FLASH memory. The memory 762 can also be volatile, such as static or dynamic RAM, and a processor, such as a microcontroller or microprocessor, can be provided to manage the electronic memory as well as the interaction between the FPGA or CPLD and the memory. In an embodiment, the reconstruction device 764 can include a CPU and a graphics processing unit (GPU) for processing and generating reconstructed images. The GPU may be a dedicated graphics card or an integrated graphics card sharing resources with the CPU, and may be one of a variety of artificial intelligence-focused types of GPUs, including NVIDIA Tesla and AMD FireStream.

Alternatively, the CPU in the reconstruction device 764 can execute a computer program including a set of computer-readable instructions that perform the functions described herein, the program being stored in any of the above-described non-transitory electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a XEON® processor from Intel® of America or an OPTERON™ processor from AMD of America and an operating system, such as Microsoft® 10, UNIX®, SOLARIS®, LINUX®, Apple MAC-OS® and other operating systems known to those skilled in the art. Further, the CPU in the reconstruction device 764 can be implemented as multiple processors cooperatively working in parallel to perform the instructions.

In one implementation, the reconstructed images can be displayed on a display 766. The display 766 can be an LCD display, CRT display, plasma display, OLED, LED, or any other display known in the art.

The memory 762 can be a hard disk drive, CD-ROM drive, DVD drive, FLASH drive, RAM, ROM, or any other electronic storage known in the art.

Obviously, numerous modifications and variations are possible in light of the above teachings. It is therefore to be understood that within the scope of the appended claims, the disclosure may be practiced otherwise than as specifically described herein.

Embodiments of the present disclosure may also be as set forth in the following parentheticals.

(1) A method for controlling X-ray emissions during three-dimensional X-ray imaging, the method including, but not limited to: obtaining a projection data set acquired in a first three-dimensional X-ray scan of a three-dimensional region of an object; obtaining a spatially-distributed characteristic of the projection data set, wherein the spatially-distributed characteristic is distributed in a longitudinal direction of the first three-dimensional X-ray scan; and controlling X-ray emissions of the three-dimensional region during a second three-dimensional X-ray scan based the spatially-distributed characteristic of the projection data.

(2) The method of (1), wherein obtaining the spatially-distributed characteristic of the projection data set includes, but is not limited to: obtaining, from the projection data set, a spatially-distributed noise characteristic spatially distributed in the longitudinal direction.

(3) The method of (1), wherein obtaining the spatially-distributed characteristic of the projection data set includes, but not limited to: obtaining, from the projection data set, a tissue-specific spatially-distributed noise characteristic spatially distributed in the longitudinal direction.

(4) The method of (1), wherein obtaining the spatially-distributed characteristic of the projection data set includes, but is not limited to: obtaining, from the projection data set, a soft-tissue-specific spatially-distributed noise characteristic spatially distributed in the longitudinal direction.

(5) The method of (4), wherein obtaining, from the projection data set, the soft-tissue-specific spatially-distributed noise characteristic spatially distributed in the longitudinal direction includes, but is not limited to: performing a first half-scan reconstruction on a first set of plural views of the projection data to produce a first reconstructed image; and performing a second half-scan reconstruction on a second set of plural views of the projection data to produce a second reconstructed image, wherein the first and second sets of plural views are different but correspond to a same position in the longitudinal direction.

(6) The method of any one of (1)-(4), wherein obtaining the spatially-distributed characteristic of the projection data set includes, but is not limited to: obtaining a first noise characteristic at a first location in the longitudinal direction from a difference between (a) a first image reconstructed from a first subset of the projection data set corresponding to the first location and (b) a second image reconstructed from a second subset of the projection data set corresponding to the first location.

(7) The method of (6), wherein obtaining the spatially-distributed characteristic of the projection data set further includes, but is not limited to: obtaining a second noise characteristic at a second location in the longitudinal direction from a difference between (a) a third image reconstructed from a third subset of the projection data set corresponding to the second location and (b) a fourth image reconstructed from a fourth subset of the projection data set corresponding to the second location, wherein the first and second locations are different.

(8) The method of any one of (2)-(4), wherein obtaining the spatially-distributed characteristic of the projection data set includes, but is not limited to: obtaining the spatially-distributed noise characteristic spatially distributed in the longitudinal direction by applying the projection data set to a neural network.

(9) The method of any one of (1)-(8), wherein obtaining the spatially-distributed characteristic of the projection data set includes, but is not limited to: obtaining, from the projection data set, a spatially-distributed organ sensitivity characteristic spatially distributed in the longitudinal direction.

(10) The method of (9), wherein obtaining the spatially-distributed characteristic of the projection data set includes, but is not limited to: obtaining, from the projection data set, a spatially-distributed and rotationally-specific organ sensitivity characteristic spatially distributed in the longitudinal direction and varying depending on an angle of an x-ray transmitter.

(11) The method of (9), wherein obtaining the spatially-distributed organ sensitivity characteristic spatially distributed in the longitudinal direction includes, but is not limited to: generating the spatially-distributed organ sensitivity characteristic spatially distributed in the longitudinal direction by applying the projection data set to a neural network.

(12) A three-dimensional X-ray imaging apparatus including, but not limited to: processing circuitry for performing the method of any one of (1)-(11).

(13) A non-transitory computer readable medium for storing computer executable instructions for causing a computer to perform a method for controlling X-ray emissions during three-dimensional X-ray imaging, the method comprising the method of any one of (1)-(11).

(14) The method of (1)-(11), the imaging apparatus of (12) performing the method of any one of (1)-(11), and the non-transitory computer readable medium for performing the method of (1)-(11), wherein the first and second three-dimensional X-ray scans include, but are not limited to, computed tomography (CT) scans, tomosynthesis scans, and VCT (X-ray volume CT) scans.

Thus, the foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A method for controlling X-ray emissions during three-dimensional X-ray imaging, the method comprising:
    obtaining a projection data set acquired in a first three-dimensional X-ray scan of a three-dimensional region of an object;
    obtaining a spatially-distributed characteristic of the projection data set, wherein the spatially-distributed characteristic is distributed in a longitudinal direction of the first three-dimensional X-ray scan; and
    controlling X-ray emissions of the three-dimensional region during a second three-dimensional X-ray scan based on the spatially-distributed characteristic of the projection data.

2. The method of claim 1, wherein obtaining the spatially-distributed characteristic of the projection data set comprises obtaining, from the projection data set, a spatially-distributed noise characteristic spatially distributed in the longitudinal direction.

3. The method of claim 1, wherein obtaining the spatially-distributed characteristic of the projection data set comprises obtaining, from the projection data set, a tissue-specific spatially-distributed noise characteristic spatially distributed in the longitudinal direction.

4. The method of claim 1, wherein obtaining the spatially-distributed characteristic of the projection data set comprises obtaining, from the projection data set, a soft-tissue-specific spatially-distributed noise characteristic spatially distributed in the longitudinal direction.

5. The method of claim 4, wherein obtaining, from the projection data set, the soft-tissue-specific spatially-distributed noise characteristic spatially distributed in the longitudinal direction comprises:
performing a first half-scan reconstruction on a first set of plural views of the projection data to produce a first reconstructed image; and
performing a second half-scan reconstruction on a second set of plural views of the projection data to produce a second reconstructed image, wherein the first and second sets of plural views are different but correspond to a same position in the longitudinal direction.

6. The method of claim 1, wherein obtaining the spatially-distributed characteristic of the projection data set comprises:
obtaining a first noise characteristic at a first location in the longitudinal direction from a difference between (a) a first image reconstructed from a first subset of the projection data set corresponding to the first location and (b) a second image reconstructed from a second subset of the projection data set corresponding to the first location.

7. The method of claim 6, wherein obtaining the spatially-distributed characteristic of the projection data set further comprises:
obtaining a second noise characteristic at a second location in the longitudinal direction from a difference between (a) a third image reconstructed from a third subset of the projection data set corresponding to the second location and (b) a fourth image reconstructed from a fourth subset of the projection data set corresponding to the second location, wherein the first and second locations are different.

8. The method of claim 2, wherein obtaining the spatially-distributed characteristic of the projection data set comprises obtaining the spatially-distributed noise characteristic spatially distributed in the longitudinal direction by applying the projection data set to a neural network.

9. The method of claim 1, wherein obtaining the spatially-distributed characteristic of the projection data set comprises obtaining, from the projection data set, a spatially-distributed organ sensitivity characteristic spatially distributed in the longitudinal direction.

10. The method of claim 9, wherein obtaining the spatially-distributed characteristic of the projection data set comprises obtaining, from the projection data set, a spatially-distributed and rotationally-specific organ sensitivity characteristic spatially distributed in the longitudinal direction and varying depending on an angle of an x-ray transmitter.

11. The method of claim 9, wherein obtaining the spatially-distributed organ sensitivity characteristic spatially distributed in the longitudinal direction comprises generating the spatially-distributed organ sensitivity characteristic spatially distributed in the longitudinal direction by applying the projection data set to a neural network.

12. A three-dimensional X-ray imaging apparatus comprising:
processing circuitry configured to:
obtain a projection data set acquired in a first three-dimensional X-ray scan of a three-dimensional region of an object;
obtain a spatially-distributed characteristic of the projection data set, wherein the spatially-distributed characteristic is distributed in a longitudinal direction of the first three-dimensional X-ray scan; and
control X-ray emissions of the three-dimensional region during a second three-dimensional X-ray scan based on the spatially-distributed characteristic of the projection data.

13. The apparatus of claim 12, wherein the processing circuitry configured to obtain the spatially-distributed characteristic of the projection data set comprises processing circuitry configured to obtain, from the projection data set, a spatially-distributed noise characteristic spatially distributed in the longitudinal direction.

14. The apparatus of claim 12, wherein the processing circuitry configured to obtain the spatially-distributed characteristic of the projection data set comprises processing circuitry configured to obtain, from the projection data set, a tissue-specific spatially-distributed noise characteristic spatially distributed in the longitudinal direction.

15. The apparatus of claim 12, wherein the processing circuitry configured to obtain the spatially-distributed characteristic of the projection data set comprises processing circuitry configured to obtain a first noise characteristic at a first location in the longitudinal direction from a difference between (a) a first image reconstructed from a first subset of the projection data set corresponding to the first location and (b) a second image reconstructed from a second subset of the projection data set corresponding to the first location.

16. The apparatus of claim 13, wherein the processing circuitry configured to obtain the spatially-distributed characteristic of the projection data set comprises processing circuitry configured to obtain the spatially-distributed noise characteristic spatially distributed in the longitudinal direction by applying the projection data set to a neural network.

17. The apparatus of claim 12, wherein the processing circuitry configured to obtain the spatially-distributed characteristic of the projection data set comprises processing circuitry configured to obtain, from the projection data set, a spatially-distributed organ sensitivity characteristic spatially distributed in the longitudinal direction.

18. A non-transitory computer readable medium for storing computer executable instructions for causing a computer to perform a method for controlling X-ray emissions during three-dimensional X-ray imaging, the method comprising:
obtaining a projection data set acquired in a first three-dimensional X-ray scan of a three-dimensional region of an object;
obtaining a spatially-distributed characteristic of the projection data set, wherein the spatially-distributed characteristic is distributed in a longitudinal direction of the first three-dimensional X-ray scan; and
controlling X-ray emissions of the three-dimensional region during a second three-dimensional X-ray scan based on the spatially-distributed characteristic of the projection data.

19. The non-transitory computer readable medium of claim 18, wherein the computer instructions for causing the computer to obtain the spatially-distributed characteristic of the projection data set comprises computer instructions for causing the computer to obtain, from the projection data set, a spatially-distributed noise characteristic spatially distributed in the longitudinal direction.

20. The method according to claim 1, wherein the first and second three-dimensional X-ray scans comprise computed tomography (CT) scans, tomosynthesis scans, and VCT (X-ray volume CT) scans.

* * * * *